US006855941B1

(12) United States Patent
Tomioka

(10) Patent No.: US 6,855,941 B1
(45) Date of Patent: Feb. 15, 2005

(54) LASER MICROSCOPE

(75) Inventor: Masaharu Tomioka, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/265,183

(22) Filed: Mar. 9, 1999

(30) Foreign Application Priority Data

Mar. 11, 1998 (JP) ........................................... 10-059892

(51) Int. Cl.[7] ............................................... G01N 21/64
(52) U.S. Cl. ............................... 250/483.1; 250/458.1; 250/459.1
(58) Field of Search ......................... 250/483.1, 458.1, 250/459.1; 359/385, 368, 589

(56) References Cited

U.S. PATENT DOCUMENTS

| | | | | |
|---|---|---|---|---|
| 4,512,660 A | * | 4/1985 | Goldberg | 356/301 |
| 5,034,613 A | * | 7/1991 | Denk et al. | 250/458.1 |
| 5,133,602 A | * | 7/1992 | Batchelder et al. | 356/364 |
| 5,252,834 A | | 10/1993 | Lin | |
| 5,289,114 A | | 2/1994 | Nakamura et al. | |
| 5,583,342 A | * | 12/1996 | Ichie | 250/459.1 |
| 5,862,287 A | * | 1/1999 | Stock et al. | 385/123 |
| 5,995,281 A | | 11/1999 | Simon et al. | |
| 6,134,010 A | * | 10/2000 | Zavislan | 250/201.3 |
| 6,169,289 B1 | * | 1/2001 | White et al. | 250/458.1 |
| 6,178,041 B1 | * | 1/2001 | Simon | 359/368 |
| 6,521,899 B1 | | 2/2003 | Wolleschensky | |

FOREIGN PATENT DOCUMENTS

| | | |
|---|---|---|
| JP | 5-503149 | 5/1993 |
| JP | 11-326775 | 11/1999 |

OTHER PUBLICATIONS

G.J. Brakenhoff et al; "Femtosecond Pulse Width Control in Microscopy by Two–Photon Absorption Autocorrelation"; Sep. 1995; pp. 253–260; Journal of Microscopy, vol. 179, Pt. 3.

* cited by examiner

Primary Examiner—John R. Lee
Assistant Examiner—Anthony Quash
(74) Attorney, Agent, or Firm—Frishauf, Holtz, Goodman & Chick, P.C.

(57) ABSTRACT

A multiphoton excitation scanning laser microscope employs a laser beam source for oscillating a pulse laser beam having a wavelength range. A multiphoton excitation phenomenon takes place in a sample irradiated with the laser beam so as to emit a fluorescent light. An optical system for forming an optical path of the laser beam includes a pre-chirp compensator, a scanning optical unit and a plurality of objective lenses differing from each other in magnification and capable of being selectively arranged on the optical path. The optical system also includes a correcting mechanism for causing the pulse width of the laser beam to be constant on a cross section of the sample in the case of selecting any of the objective lenses. The correcting mechanism includes a plurality of correcting plates capable of being selectively arranged on the optical path.

18 Claims, 3 Drawing Sheets

LASER MICROSCOPE

BACKGROUND OF THE INVENTION

The present invention relates to a laser microscope of the type that a target sample to be observed is irradiated with a pulse laser beam, particularly, to a multiphoton excitation scanning laser microscope for detecting the chemical reaction and fluorescent light caused by the multiphoton absorption of the sample.

In the multiphoton excitation method, the excitation which is performed in general by a single photon, is carried out by multiphoton. In, for example, a two-photon excitation method, the fluorescent light excitation, which is performed under a wavelength of 400 nm in the case of using a single photon, is carried out under a wavelength of 800 nm which is two times as long as the wavelength for the case of using a single photon.

Generally, in a mercury lamp or a continuous oscillation laser used in a fluorescent microscope, the photon density per unit time is low, leading to requirement of a tremendous light intensity for bringing about a multiphoton excitation phenomenon. Further, it is difficult to put the multiphoton excitation method to practical use unless the problem that a damage done to the optical system or to the sample is increased is solved.

Under the circumstances, a source, which can oscillate a pulse laser beam of, for example, sub-picosecond, is used as a light beam source of the multiphoton excitation method. This is because the multiphoton excitation phenomenon takes place in a probability which is substantially proportional to the square of the light density per unit area and unit time. In the pulse laser beam of a sub-picosecond, the probability of presence of a plurality of photons is increased.

For example, PCT National Publication No. 5-503149 discloses a two-photon excitation scanning laser microscope which employs a combination of a laser beam. source for emitting a pulse laser beam of sub-picosecond and a scanning optical unit for scanning the surface of a sample (the focal plane) with the pulse laser beam emitted from the laser beam source.

Pulse laser beams of sub-picosecond emitted from a laser beam source used for the multiphoton excitation do not have a wavelength of a complete single color, but has a wavelength range correlated with the pulse width. Generally, where light passes through an optical system, the speed of light within the medium is decreased with decrease in the wavelength and is increased with increase in the wavelength. It follows that, if a pulse laser beam having a wavelength range passes through an optical system, a difference in the passing time through the optical system is brought about, depending on different wavelengths. As a result, the pulse width after the passing through the optical system is expanded in the time axis direction, compared with the pulse width before the incidence on the optical system.

Since the probability of generation of the multiphoton excitation phenomenon is dependent on the photon density, the expansion of the pulse width on the sample surface or focal plane of the optical system lowers the probability of generation of the multiphoton excitation phenomenon. Accordingly, it is preferable to prevent the pulse width on the sample surface from expanding, as far as possible.

A so-called "pre-chirp compensation" is known as a general method of solving the above-noted problem. In the pre-chirp compensation, a pulse laser beam is passed through a prism pair or a grating pair so as to allow the light having a shorter wavelength to pass through the prisms or the gratings earlier than the light having a longer wavelength. In other words, the speed of light having a longer wavelength is retarded by the pre-chirp compensation.

The pre-chirp compensation is described in, for example, "Femtosecond pulse width control in microscopy by two-photon absorption autocorrelation; G. J. Brakenhoff, M. Muller & J. Squier; J. of Microscopy, Vol. 179, Pt. 3, September 1995, pp. 253–260. This literature teaches that the pulse width of a pulse laser beam can be optionally varied on a sample surface by controlling the position of the prism pair or the grating pair used as a pre-chirp compensator.

However, where the multiphoton excitation scanning laser microscope includes a plurality of objective lenses which are used selectively, the necessary degree of correction to be performed by the pre-chirp compensator is made different, depending on the object lenses, because the objective lenses differ from each other in the optical path length. Therefore, even if the pre-chirp compensator is adjusted to minimize the pulse width of the pulse laser beam on the sample surface on the basis of a single objective lens, the pulse width on the sample surface is increased in the case of another objective lens. Incidentally, the term "optical path length" used in this specification represents the optical length of a optical path formed by a optical element, not the geometrical length of the optical element.

In general, in a scanning laser microscope of this type, a target object in the sample is detected first by using an objective lens having a low magnification and capable of observation over a wide area, followed by using an objective lens of a high magnification for observation of fine portions, as in an ordinal general microscopic observation. If the pulse width of the pulse laser beam on the sample surface is changed by the switching of the objective lenses, it is impossible to cause the multiphoton excitation phenomenon under the optimum conditions.

If the difficulty is dealt with by the adjustment of a pre-chirp compensator, another problem is generated that the fluorescent light generated from the sample is faded in proportion to the time spent for the adjustment. As a countermeasure for preventing the fluorescent light of the sample from being faded, it is considered effective to move the sample from within the observation view field during the adjustment of the pre-chirp compensator. In this method, however, the sample must be moved again back into the observation view field after the adjustment of the pre-chirp compensator. What should be noted is that it is difficult to move the sample back exactly to the original position. It follows that this method is not practical for the observation and measurement.

BRIEF SUMMARY OF THE INVENTION

An object of the present invention is to provide a multiphoton excitation scanning laser microscope, which allows observation easily under the optimum conditions, in accordance with the optical path length of an optical member selectively arranged on an optical path.

According to a first aspect of the present invention, there is provided a multiphoton excitation scanning laser microscope, comprising:

(a) a station for placing a sample to be observed;

(b) a laser beam source for emitting a pulse laser beam for exciting the sample to cause the sample to emit a fluorescent light by multiphoton excitation phenomenon;

(c) a detector for detecting the fluorescent light; and (d) an optical system for forming an optical path of the pulse laser beam for guiding the pulse laser beam from the laser beam source to the sample, the optical system including a pre-chirp compensator arranged on the optical path for preventing a pulse width of the pulse laser beam from widening due to a wavelength range of the pulse when the pulse laser beam passes through the optical system, a plurality of objective lenses capable of being selectively arranged on the optical path for collecting the pulse laser beam on the sample, and a correcting mechanism including optical correcting means for correcting an optical path length of the optical path to cause the pulse width of the pulse laser beam to be constant on a focal plane of the optical system in accordance with respective optical path lengths of the objective lenses.

According to a second aspect of the present invention, there is provided a multiphoton excitation scanning laser microscope, comprising:

(a) a station for placing a sample to be observed;

(b) a laser beam source for emitting a pulse laser beam for exciting the sample to cause the sample to emit a fluorescent light by multiphoton excitation phenomenon;

(c) a detector for detecting the fluorescent light; and (d) an optical system for forming an optical path of the pulse laser beam for guiding the pulse laser beam from the laser beam source to the sample, the optical system including a pre-chirp compensator arranged on the optical path for preventing a pulse width of the pulse laser beam from widening due to a wavelength range of the pulse when the pulse laser beam passes through the optical system, an optical member selectively arranged on the optical path, and a correcting mechanism including optical correcting means for correcting an optical path length of the optical path to cause the pulse width of the pulse laser beam to be constant on a focal plane of the optical system in accordance with an optical path length of the optical member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
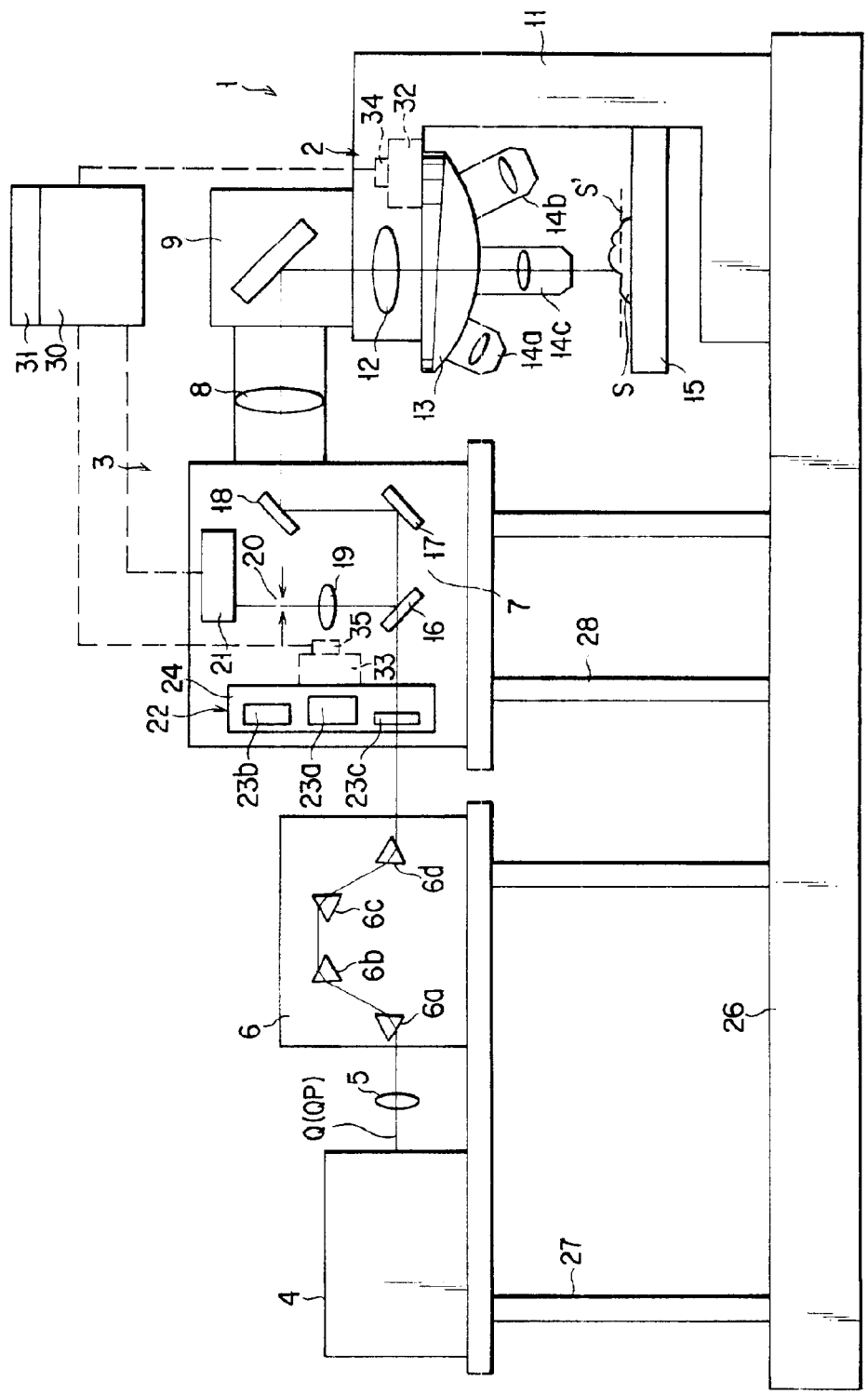
FIG. 1 shows the construction of a multiphoton excitation scanning laser microscope according to one embodiment of the present invention.

Embodiments of the present invention will be described hereinafter with reference to the accompanying drawing. In the following description, the constituent elements having substantially the same function and arrangement are denoted by the same reference numerals, and a repetitive description will be made only when necessary.

Specifically, FIG. 1 shows the construction of a multiphoton excitation scanning laser microscope 1 according to one embodiment of the present invention.

The microscope 1 comprises a laser beam source 4 for emitting a pulse laser beam for irradiating a sample S, and an optical system 3 forming an optical path for guiding the laser beam from the laser beam source 4 to the sample S. The optical system 3 is formed of a large number of optical elements including the optical elements within a microscope body 2 having a stage 15 on which the sample S is disposed.

The microscope 1 is arranged on a vibration eliminating base 26 for eliminating the vibration transmitted from the floor. Two rests 27 and 28 are mounted to the base 26. Arranged on the rest 27 are a laser beam source 4, a beam collimator 5 and a pre-chirp compensator 6. On the other hand, a scanning optical unit 7 and a correcting mechanism 22 are mounted on the rest 28. The scanning optical unit 7 and a photomultiplier 21 described later are connected to a computer 30 having an operation panel 31.

The laser beam source 4 oscillates extremely short pulses QP of sub-picosecond with near infrared wavelengths. Since, the breadth of the wavelength range is inversely proportional to the pulse width, the extremely short pulse QP used in this embodiment has a wavelength range of about several nanometers.

The beam collimator 5 and the pre-chirp compensator 6 are arranged on the optical path of the laser beam Q emitted from the laser beam source 4. The beam collimator 5 collimates the laser beam Q emitted from the laser beam source 4 into a parallel luminous flux. The pre-chirp compensator 6 is used for performing such an adjustment in advance that the widening of the pulse width due to the wavelength range of the pulse is canceled, while the laser beam Q passes through the optical system 3. To be more specific, the pre-chirp compensator 6 consists of optical elements 6a to 6d such-as prisms and serves to cause the collimated laser beam Q incoming into the pre-chirp compensator 6 to be emitted from the pre-chirp compensator 6 in the order of the wavelength such that the shorter the wavelength is, the earlier it is emitted.

The scanning optical unit 7 moves the laser beam Q emitted from the pre-chirp compensator 6 so as to allow a cross section (focal plane) S' of the sample S to be scanned by the image of the laser beam Q. The microscope body 2 is arranged on the outlet side of the scanning optical unit 7 with a relay lens 8 and an optical path bending unit 9 interposed therebetween. These relay lens 8, the optical path bending unit 9 and the microscope body 2 are arranged such that their optical axes are coincident.

The microscope body 2 includes a C-shaped frame 11 fixed to the vibration eliminating base 26. An image forming lens 12 is arranged on an upper portion of the C-shaped frame 11. Also, a revolver 13, on which a plurality of objective lenses differing from each other in magnification, e.g., three objective lenses 14a, 14b, and 14c, are mounted, is rotatably arranged below the image forming lens 12. These objective lenses 14a, 14b, and 14c can be selectively arranged on the optical axis. The stage 15 supporting the sample S is arranged below the revolver 13. It is possible to adjust the vertical position of the stage 15 relative to the frame 11.

When the sample S is irradiated with an extremely short pulse QP of the laser beam Q, the sample S is caused to emit a fluorescent light by the multiphoton excitation phenomenon. A dichroic mirror 16 is arranged within the scanning optical unit 7 for separating the fluorescent light generated from the sample S from the laser beam Q coming from the pre-chirp compensator 6.

A pair of galvano mirrors 17 and 18 for moving the laser beam Q for scanning in directions perpendicular to each other are arranged on the optical path of the laser beam Q transmitted through the dichroic mirror 16. The relay lens 8 is arranged to guide the laser beam Q moved for scanning toward the microscope body 2.

On the other hand, a light collecting lens 19, a pin hole 20, and the photomultiplier 21 are arranged on the optical path for detecting the fluorescent light separated from the dichroic mirror 16. The light collecting lens 19 is used for collecting the fluorescent light emitted from the sample S onto the pin hole 20. The pin hole 20 is arranged at a conjugated position relative to the sample S, so as to remove the unnecessary light generated from portions other than the focal plane and included in the light from the sample. Incidentally, in a multiphoton excitation scanning microscope, the multiphoton excitation phenomenon takes place only at the focal plane of each of the objective lenses 14a, 14b, and 14c, i.e., only at the cross section S' of the sample S. Therefore, the pin hole 20 is not absolutely necessary for the scanning optical unit 7.

The objective lenses 14a, 14b, and 14c differ from each other in the optical path length. Thus, even if the pre-chirp compensator 6 is adjusted to minimize the pulse width of the extremely short pulse QP on the cross section S' of the sample (i.e., focal plane of the optical system 3) in accordance with a single objective lens, the pulse width on the cross section S' of the sample may be widened in the case of another objective lens. The correcting mechanism 22 is arranged to deal with this problem. Specifically, the correcting mechanism 22 is arranged to correct the optical path length of the optical system 3 so as to cause the pulse width to be constant and minimum on the cross section S' of the sample in the case of selecting any of the objective lenses 14a, 14b and 14c. As described previously, the term "optical path length" used in this specification represents the optical length of a optical path formed by a optical element, not the geometrical length of the optical element.

To be more specific, the correcting mechanism 22 the scanning optical unit 7 are commonly arranged within the same casing in this embodiment of the present invention. The correcting mechanism 22 comprises correcting plates 23a, 23b, and 23c which can be selectively arranged on the optical path of the laser beam Q collimated into a parallel luminous flux. These correcting plates 23a, 23b, and 23c are formed of the same glass material and have optical path lengths set to conform with the objective lenses 14a, 14b, and 14c, respectively. These objective lenses 14a, 14b, and 14c and the corresponding correcting plates 23a, 23b, and 23c form three pairs. In the case of using any of these pairs, the optical path length from the laser beam source 4 to the cross section S' of the sample S is set to be the same.

Figure 2:
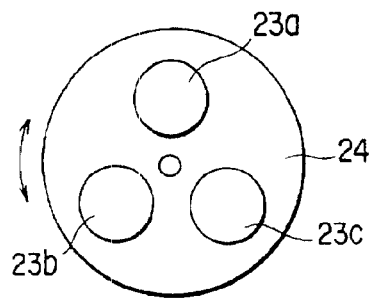
FIG. 2 is a plan view schematically showing the mechanism of correcting optical path length, the correcting mechanism being used in the microscope shown in FIG. 1.

As shown in FIG. 2, the correcting plates 23a, 23b, and 23c are mounted to a rotatable turret 24. These correcting plates 23a, 23b, and 23c can be selectively arranged on the optical axis of the optical system 3 by rotating the turret 24.

Let us describe the operation of the multiphoton excitation scanning laser microscope shown in FIG. 1.

Specifically, the pulse laser beam Q of extremely short pulses QP emitted from the laser beam source 4 is first converted into a parallel luminous flux by the beam collimator 5. Then, the laser beam Q comes in the pre-chirp compensator 6 and is adjusted thereby to have the minimum laser pulse width on the cross section S' of the sample S. Then, the laser beam Q is introduced into the scanning optical unit 7.

Then, the laser beam Q thus introduced into the scanning optical unit 7 passes through one of the correcting plates 23a, 23b, and 23c corresponding to the objective lenses 14a, 14b, and 14c, respectively. For example, the laser beam Q passes the correcting plates 23a corresponding to the objective lens 14a, so that it is reshaped in accordance with the objective lens 14a to allow the pulse width on the cross section S' to be constant.

Further, the laser beam Q is incident on the dichroic mirror 16 included in the scanning optical unit 7. The laser beam Q transmitted through the dichroic mirror 16 is reflected from the pair of galvano mirrors 17 and 18 and, then, passes through the relay lens 8 and the optical path bending unit 9 so as to be incident on the optical system of the microscope body 2.

The laser beam Q incident on the microscope body 2 is converted into a luminous flux by the image forming lens 12, such that the luminous flux having a diameter satisfying the pupil diameter of one of the objective lenses 14a, 14b, and 14c, e.g., the objective lens 14a, and introduced into the objective lens 14a. The laser beam Q thus introduced into the objective lens 14a is collected by the objective lens 14a on the cross section S' of the sample S disposed on the stage 15.

Upon irradiation with pulse the laser beam Q, the sample S is partly excited by the two-photon excitation phenomenon at the cross section S'. As a result, a fluorescent light conforming with a dyed fluorescent coloring matter is emitted from the cross section S' of the sample S. The fluorescent light thus emitted is taken again into the objective lens 14a and passes through the image forming lens 12, the optical path bending unit 9, the relay lens 8 and the pair of galvano mirrors 18 and 17 so as to be incident on the dichroic mirror 16 and separated from the pulse laser beam Q.

The fluorescent light is reflected by the dichroic mirror 16 and, then, collected by the light collecting lens 19 on the pin hole 20. It should be noted that only the fluorescent light which has passed through the pin hole 20 is incident on the photomultiplier 21. Upon receipt of the fluorescent light, the photomultiplier 21 supplies an electric signal conforming with the received amount of the fluorescent light to the computer 30.

During the operation described above, the pair of galvano mirrors 17 and 18 included in the scanning optical unit 7 are driven in X-Y directions so as to have the cross section S' of the sample S scanned by the laser beam Q in the X-Y directions. The output signal of the photomultiplier 21 obtained by this scanning is processed in the computer 30 in synchronism with the scan-driving of the galvano mirrors 17 and 18. As a result, a two dimensional image of the cross section S' of the sample S is formed.

In order to obtain the two dimensional image of the sample S, as described above, the objective lens 14a may be switched to the objective lens 14c (or objective lens 14b) by rotating the revolver 13, as the case may be. In this case, the turret 24 of the correcting mechanism 22 is rotated substantially simultaneously with the switching of the objective lens so as to dispose the correcting plate 23c corresponding to the objective lens 14c on the optical path of the laser beam Q, which has been collimated to be a parallel luminous flux.

As described above, where the correcting plates 23a, 23b, and 23c are combined with the corresponding objective lenses 14a, 14b, and 14c, respectively, the pulse width of the laser beam Q on the cross section S' of the sample S is set constant. It follows that, if the pulse width on the cross section S' of the sample S is adjusted to be minimum in the initial stage (set up stage of the apparatus) by using, for example, the objective lens 14a and the correcting plate 23a, adjustment of the pre-chirp compensator 6 is rendered unnecessary even in the case of using another pair of the objective lens and the correcting plate. In other words, the pulse width on the cross section S' of the sample S is always constant and minimum in the case of using any of the pairs of the objective lenses 14a, 14b, and 14c and the correcting plates 23a, 23b, and 23c.

As described above, in the multiphoton excitation scanning laser microscope shown in FIG. 1, the multiphoton excitation phenomenon can be caused under the optimum conditions in the case of switching and using any of the objective lenses 14a, 14b, and 14c. Also, since the observation can be started instantly under the optimum state, the fading of the fluorescent light can be suppressed to a minimum level, leading to an improved working efficiency. It should also be noted that, since each of the correcting plates 23a, 23b, and 23c is positioned on the optical path of the laser beam Q collimated into a parallel luminous flux, each of these correcting plates 23a, 23b, and 23c does not deteriorate the performance of each of the objective lenses 14a, 14b, and 14c, making it possible to maintain easily the optical performance of the entire system.

It should also be noted that the switching of the correcting plates 23a, 23b, and 23c can be interlocked electrically or mechanically with the switching of the objective lenses 14a, 14b, and 14c, in place of manual operation. In this case, the operation of the apparatus is simplified so as to improve the working efficiency and, at the same time, to prevent each of the correcting plates 23a, 23b, and 23c from being inserted erroneously. For example, the electrical interlocking mechanism is denoted by broken lines in FIG. 1.

In the interlocking mechanism shown in FIG. 1, the revolver 13 and the turret 24 are driven by step motors 32 and 33, respectively. Also, encoders 34, 35 are joined to the rotary shafts of these step motors 32, 33, respectively. These members 32 to 35 are connected to the computer 30. Also, an operation panel 31 for determining which of the objective lenses 14a, 14b, and 14c is to be used is mounted to the computer 30. It follows that the objective lenses 14a, 14b, and 14c and the correcting plates 23a, 23b, and 23c can be automatically switched in an interlocking manner based on the input signal supplied to the operation panel 31.

Other than the above described mechanisms, the following modification may be adopted. Specifically, the positions and magnifications of objective lenses mounted on a revolver are set in advance, and when the revolver is manually rotated, a correcting plate corresponding to a selected objective lens is identified, thereby switching correcting plates.

It is desirable for the correcting plates 23a, 23b, and 23c to be arranged on that portion of the optical path in which the laser beam Q forms a parallel luminous flux and there is no change in the angle of the luminous flux, e.g., the portion between the laser beam source 4 and the dichroic mirror 16. To be more specific, the correcting plates 23a, 23b, and 23c may be arranged, for example, at the position between the beam collimator 5 and the pre-chirp compensator 6, in place of the position between the pre-chirp compensator 6 and the scanning optical unit 7 shown in FIG. 1.

Figure 3:
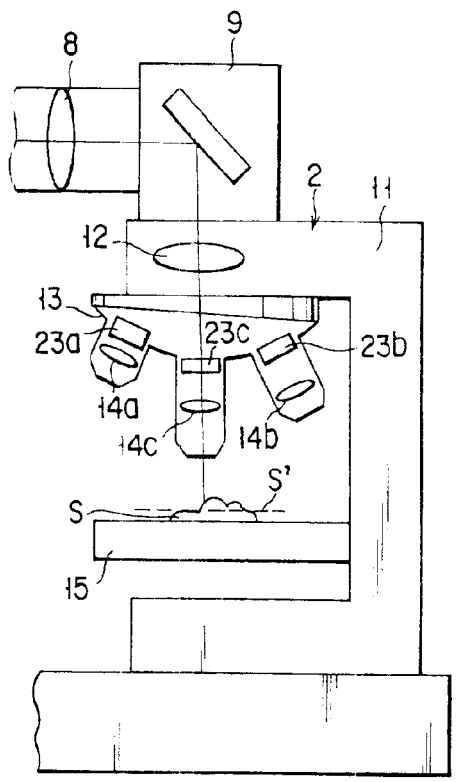
FIG. 3 is a side view schematically showing a modification of the correcting mechanism of optical path length.

If the optical system of each of the objective lenses 14a, 14b, and 14c forms an infinite system, each of the correcting plates 23a, 23b, and 23c can be arranged within the revolver 13 or the objective lenses, as shown in FIG. 3, so as to form a mechanical interlocking mechanism. This arrangement simplifies the construction of the apparatus and lowers the manufacturing cost of the apparatus, and a malfunctional operation of the apparatus need not be worried about.

In the above described embodiment, the correcting plates are formed of the same glass material, but has different thickness, so that they have different optical path length. The present invention is not limited to this arrangement. For example, the correcting plates can be formed of the same thickness while their glass materials being different to have different refractive indices so as to set a desired optical path length. Where the correcting plates 23a, 23b, and 23c are formed in this fashion, these correcting plates are exactly the same in the geometrical size, making it possible to use common parts for mounting the correcting plates to the correcting mechanism 22.

Figure 4:
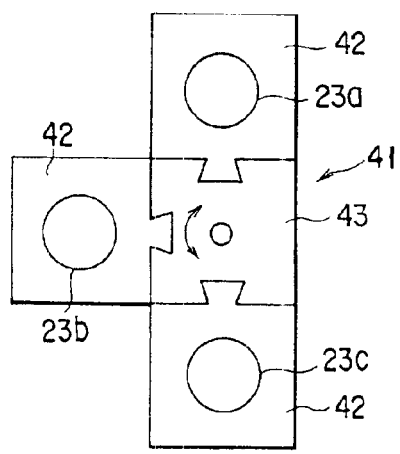
FIG. 4 is a plan view schematically showing another modification of the correcting mechanism of optical path length.
Figure 5:
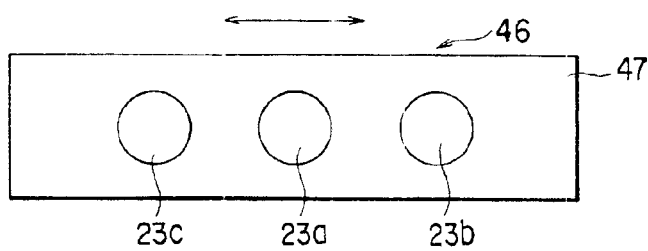
FIG. 5 is a plan view schematically showing another modification of the correcting mechanism of optical path length.
Figure 6:
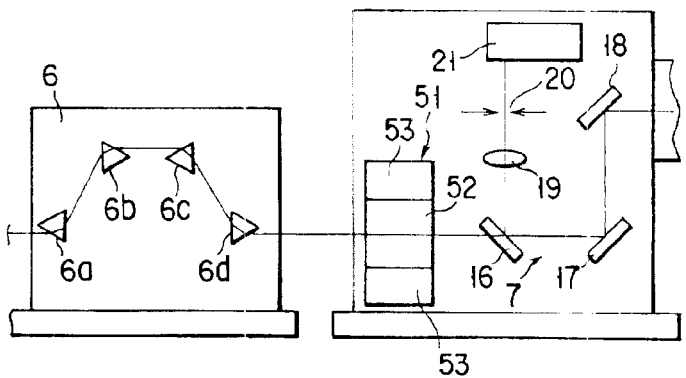
FIG. 6 is a side view schematically showing still another modification of the correcting mechanism of optical path length.

FIGS. 4 to 6 schematically show correcting mechanisms 41, 46 and 51, respectively, according to modifications of the correcting mechanism 22.

The correcting mechanism 41 shown in FIG. 4 is a modification in which the correcting plates 23a, 23b, and 23c are mounted respectively to rectangular blocks 42 which are detachably mounted to a rectangular rotor 43. In this modification, the correcting plates 23a, 23b, and 23c can be selectively positioned on the optical axis of the optical system 3 by rotating the rotor 43.

The correcting mechanism 46 shown in FIG. 5 is a modification in which the correcting plates 23a, 23b, and 23c are mounted to a slidable slider 47. In this modification, the correcting plates 23a, 23b, and 23c can be selectively positioned on the optical axis of the optical system 3 by linearly moving the slider 47.

Further, in the correcting mechanism 51 shown in FIG. 6, used is a single optical correcting element 52 capable of selectively providing different optical path lengths on the optical path under an electrical or physical external action produced by a driving section 53. A parallel plain plate (EOD element) in which optical path length is changed upon application of different voltages or a parallel plain plate in which optical path length is changed by means of photoelasticity upon application of different pressures can be used as the optical correcting element 52.

Figure 7:
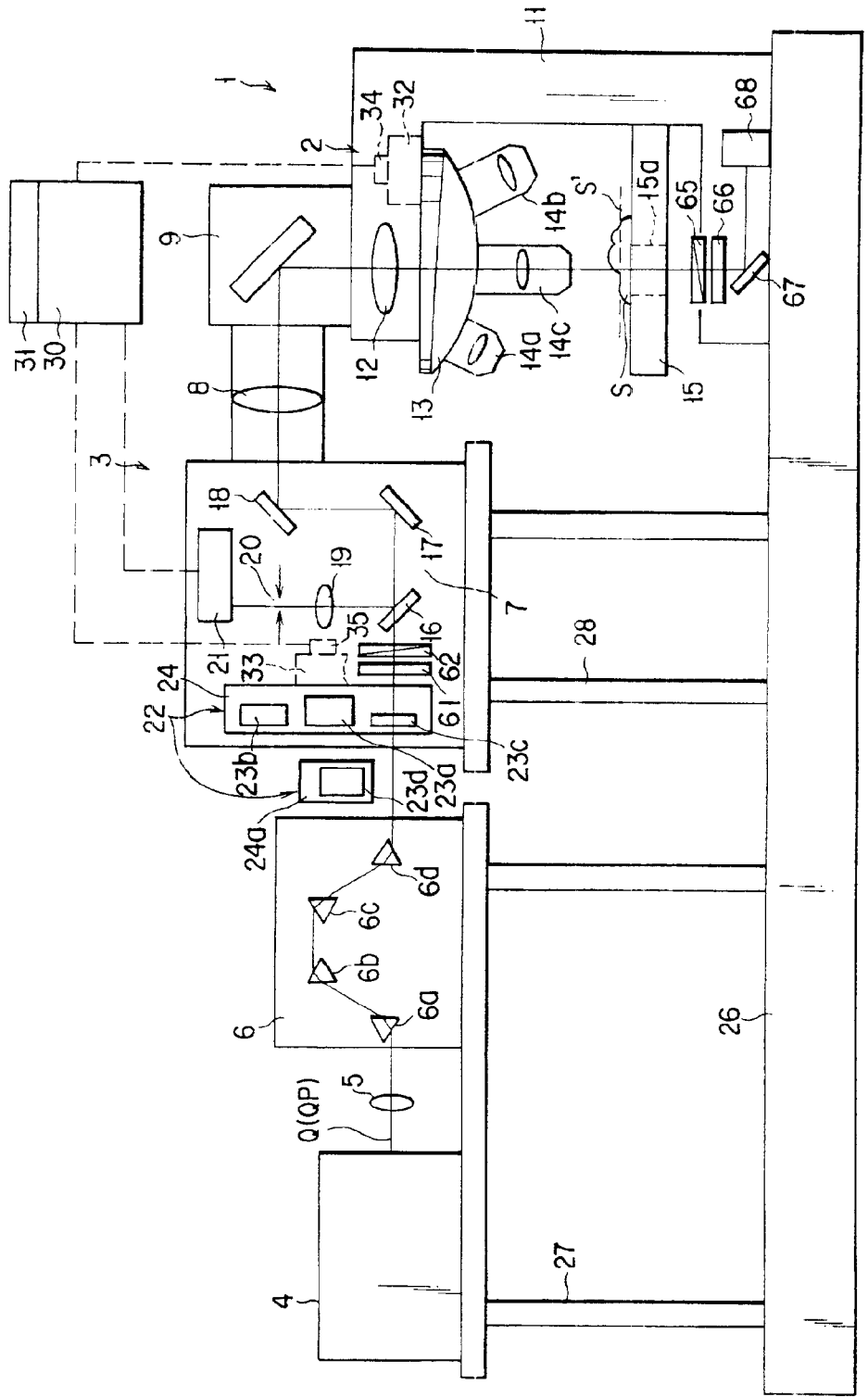
FIG. 7 schematically shows a modification in which a function for a Nomarski observation of transmitted light is added to the microscope shown in FIG. 1.

FIG. 7 schematically shows a modification in which a function for a Nomarski observation of transmitted light is added to the microscope shown in FIG. 1.

In this modification, a light polarizer 61 and a birefringence element 62 represented by Nomarski prism are attached to a slider (not shown), and integratedly inserted onto and withdrawn from the optical path in the scanning optical unit 7, on the side of dichroic mirror 16 close to the pre-chirp compensator 6. In this case, when the light polarizer 61 and the birefringence element 62 are withdrawn form the optical path because only the detection of the fluorescent light by the photomultiplier 21 is required, the optical path length of the optical path can be changed. In order to solve this problem, a correcting plate 23*d* corresponding to the optical path length of the light polarizer 61 and the birefringence element 62 is attached to a slider 24*a*, which is independent of the turret 24, but constitutes part of the correcting mechanism 22. The correcting plate 23*d* is inserted onto the optical path to be interlocked with withdrawal of the light polarizer 61 and the birefringence element 62 from the optical path.

Also, a birefringence element (Nomarski prism) 65 and an polarizer 66 are mounted in a lower portion of the frame 11 of the microscope body 2 in a manner to be positioned below an opening 15*a* of the stage 15. Further, a mirror 67 and a detector 68 are mounted within the frame 11 of the microscope 2. The light passing through the polarizer 66 is reflected by the mirror 67 and, then, detected by the detector 68.

The light polarizer 61, the birefringence elements 62, 65 and the polarizer 66 serve to visualize the phase information which cannot be visually detected such as a colorless and transparent substance having a slight local difference in refractive index or a surface of an opaque substance having fine steps by imparting contrast of interference colors to the phase information by utilizing polarization and interference. It follows that the construction of the sample S can be grasped in three dimensions from the information obtained from the transmitted light detected by the detector 68 in addition to the information obtained from the fluorescent light detected by the photomultiplier 21.

When only the detection of the fluorescent light by the photomultiplier 21 is required, the light polarizer 61 and the birefringence element 62 on the upper side can be moved away from the optical path. To be interlocked with this, the correcting plate 23*d* corresponding to the optical path length of the light polarizer 61 and the birefringence element 62 is inserted onto the optical path. With this operation, it is possible to cause the pulse width to be constant and minimum on the cross section S' of the sample, in the microscope in which the Nomarski observation of transmitted light and the detection of the fluorescent light by the photomultiplier 21 can be switchedly performed. Note that, in place of the structure shown in FIG. 7, correcting plates (not shown) formed in consideration of the optical path length of the light polarizer 61 and the birefringence element 62 may be arranged on the turret 24 in addition to the correcting plates 23*a*, 23*b*, and 23*c*.

In the above described embodiment and modifications, the scanning optical unit 7 including the pair of galvano mirrors 17 and 18, and the like, for running the pulse laser beam Q is used as a scanning mechanism for scanning the sample S with the laser beam Q. However, the scanning of the sample S is achieved by moving the sample S and the pulse laser beam Q relative to each other, and thus any one of various mechanisms can be adopted for this scanning operation. For example, it is possible to employ a scanning mechanism in which the pulse laser beam Q is stationary while the stage 15 of the microscope body 2 is driven for the scanning operation.

As described above, the present invention provides a multiphoton excitation scanning laser microscope using a pulse laser beam and including a plurality of objective lenses. The laser microscope of the present invention allows observation easily under the optimum conditions, in accordance with the optical path length of an optical member selectively arranged on an optical path.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A multiphoton excitation scanning laser microscope, comprising:
   (a) a station for placing a sample to be observed;
   (b) a laser beam source for emitting a pulse laser beam for exciting said sample to cause the sample to emit a fluorescent light by multiphoton excitation phenomenon;
   (c) a detector for detecting said fluorescent light; and
   (d) an optical system for forming an optical path of said pulse laser beam for guiding said pulse laser beam from said laser beam source to said sample, said optical system including:
      a pre-chirp compensator disposed on said optical path such that the pulse laser beam passes therethrough, and preset to provide said pulse laser beam with a certain amount of pre-chirp compensation, said pre-chirp compensator comprising optical elements which cause components of the pulse laser beam to be emitted in order of wavelength such that shorter wavelengths are emitted earlier than longer wavelengths;
      a plurality of objective lenses adapted to be selectively placed on said optical path for collecting the pulse laser beam on the sample, the objective lenses including objective lenses having different optical path lengths,
      a revolver for switching the objective lenses, and
      a correcting mechanism for correcting an optical path length of said optical path so as to be constant no matter which of said objective lenses is selectively placed on said optical path,
      wherein said correcting mechanism comprises at least one flat optical correcting element adapted to be selectively inserted in said optical path in accordance with which of said objective lenses is selectively placed on said optical path, so as to maintain the optical path length of the optical system without moving said optical elements of said pre-chirp compensator, and
      wherein said certain amount of pre-chirp compensation provided by said pre-chirp compensator is set to prevent a pulse width of said pulse laser beam from widening due to a wavelength range of a pulse of said pulse laser beam when said pulse laser beam passes through said optical path whose optical path length is kept constant.

2. The microscope according to claim 1, further comprising an interlocking mechanism for causing operation of said correcting mechanism to be interlocked with switchover of said objective lenses.

3. The microscope according to claim 1, wherein said at least one optical correcting element is adapted to be arranged on said optical path at a position where said pulse laser beam forms a parallel luminous flux and there is no change in an angle of said luminous flux.

4. The microscope according to claim 1, wherein said correcting mechanism includes a rotor supporting said at least one optical correcting element.

5. The microscope according to claim 1, wherein said correcting mechanism includes a slider supporting said at least one optical correcting element.

6. The microscope according to claim 1, wherein said at least one optical correcting element and said objective lenses are supported by a same supporting member and are moved together.

7. The microscope according to claim 1, wherein said optical system further comprises a scanning mechanism for scanning said sample to be observed with said pulse laser beam.

8. The microscope according to claim 7, wherein said scanning mechanism comprises a scanning optical unit for moving said pulse laser beam, and wherein said at least one optical correcting element is adapted to be arranged on said optical path at a position between said scanning optical unit and said pre-chirp compensator.

9. The microscope according to claim 1, wherein said optical system also forms an optical path for guiding said fluorescent light to said detector.

10. The microscope according to claim 1, further comprising an additional optical system and detector for detecting light of the pulse laser beam that is transmitted through the sample.

11. A multiphoton excitation scanning laser microscope, comprising:
   (a) a station for placing a sample to be observed;
   (b) a laser beam source for emitting a pulse laser beam for exciting said sample to cause the sample to emit a fluorescent light by multiphoton excitation phenomenon;
   (c) a detector for detecting said fluorescent light; and
   (d) an optical system for forming an optical path of said pulse laser beam for guiding said pulse laser beam from said laser beam source to said sample, said optical system including:
      a pre-chirp compensator disposed on said optical path such that the pulse laser beam passes therethrough, and preset to provide said pulse laser beam with a certain amount of pre-chirp compensation, said pre-chirp compensator comprising optical elements which cause components of the pulse laser beam to be emitted in order of wavelength such that shorter wavelengths are emitted earlier than longer wavelengths,
      an optical member adapted to be selectively placed on said optical path, the optical member including a plurality of members having different optical path lengths, and
      a correcting mechanism for correcting an optical path length of said optical path so as to be constant,
   wherein said correcting mechanism comprises at least one flat optical correcting element adapted to be selectively inserted in said optical path in accordance with selective placement of said optical member, so as to maintain the optical path length of the optical system without moving said optical elements of said pre-chirp compensator, and
   wherein said certain amount of pre-chirp compensation provided by said pre-chirp compensator is set to prevent a pulse width of said pulse laser beam from widening due to a wavelength range of a pulse of said pulse laser beam when said pulse laser beam passes through said optical path whose optical path length is kept constant.

12. The microscope according to claim 11, wherein said optical member comprises a plurality of objective lenses adapted to be selectively placed on said optical path for collecting the pulse laser beam on the sample.

13. The microscope according to claim 11, wherein said optical member comprises a plurality of objective lenses adapted to be selectively placed on said optical path for collecting the pulse laser beam on the sample, and said optical member includes said correcting mechanism, which is adapted to be selectively inserted between said pre-chirp compensator and said objective lenses.

14. The microscope according to claim 13, wherein said optical element comprises a Nomarski prism.

15. A multiphoton excitation scanning laser microscope, comprising:
   (a) a station for placing a sample to be observed;
   (b) a laser beam source for emitting a pulse laser beam for exciting said sample to cause the sample to emit a fluorescent light by multiphoton excitation phenomenon;
   (c) a detector for detecting said fluorescent light; and
   (d) an optical system for forming an optical path of said pulse laser beam for guiding said pulse laser beam from said laser beam source to said sample, said optical system including:
      a pre-chirp compensator disposed on said optical path such that the pulse laser beam passes therethrough, and preset to provide said pulse laser beam with a certain amount of pre-chirp compensation, said pre-chirp compensator comprising optical elements which cause components of the pulse laser beam to be emitted in order of wavelength such that shorter wavelengths are emitted earlier than longer wavelengths,
      a plurality of objective lenses adapted to be selectively placed on said optical path for collecting the pulse laser beam on the sample, the objective lenses including objective lenses having different optical path lengths,
      a revolver for switching the objective lenses, and
      a correcting mechanism for causing an optical path length of said optical path to be constant no matter which of said objective lenses is selectively placed on said optical path,
   wherein said correcting mechanism comprises a parallel plain plate whose optical path length is adjustable by applying different voltages in accordance with which of said objective lenses is selectively placed on said optical path, so as to maintain the optical path length of the optical system without moving said optical elements of said pre-chirp compensator, and
   wherein said certain amount of pre-chirp compensation provided by said pre-chirp compensator is set to prevent a pulse width of said pulse laser beam from widening due to a wavelength range of a pulse of said pulse laser beam when said pulse laser beam passes through said optical path whose optical path length is kept constant.

16. A multiphoton excitation scanning laser microscope, comprising:
   (a) a station for placing a sample to be observed;

(b) a laser beam source for emitting a pulse laser beam for exciting said sample to cause the sample to emit a fluorescent light by multiphoton excitation phenomenon;

(c) a detector for detecting said fluorescent light; and (d) an optical system for forming an optical path of said pulse laser beam for guiding said pulse laser beam from said laser beam source to said sample, said optical system including:

a pre-chirp compensator disposed on said optical path such that the pulse laser beam passes therethrough, and preset to provide said pulse laser beam with a certain amount of pre-chirp compensation, said pre-chirp compensator comprising optical elements which cause components of the pulse laser beam to be emitted in order of wavelength such that shorter wavelengths are emitted earlier than longer wavelengths, a plurality of objective lenses adapted to be selectively placed on said optical path for collecting the pulse laser beam on the sample, the objective lenses including objective lenses having different optical path lengths, a revolver for switching the objective lenses, and a correcting mechanism for causing an optical path length of said optical path to be constant no matter which of said objective lenses is selectively placed on said optical path, wherein said correcting mechanism comprises a parallel plain plate whose optical path length is adjustable by applying different pressures in accordance with which of said objective lenses is selectively placed on said optical path, so as to maintain the optical path length of the optical system without moving said optical element of said pre-chirp compensator, and wherein said certain amount of pre-chirp compensation provided by said pre-chirp compensator is set to prevent a pulse width of said pulse laser beam from widening due to a wavelength range of a pulse of said pulse laser beam when said pulse laser beam passes through said optical path whose optical path length is kept constant.

17. A multiphoton excitation scanning laser microscope, comprising:

(a) a station for placing a sample to be observed;

(b) a laser beam source for emitting a pulse laser beam for exciting said sample to cause the sample to emit a fluorescent light by multiphoton excitation phenomenon;

(c) a detector for detecting said fluorescent light; and (d) an optical system for forming an optical path of said pulse laser beam for guiding said pulse laser beam from said laser beam source to said sample, said optical system including:

a pre-chirp compensator disposed on said optical path such that the pulse laser beam passes therethrough, and preset to provide said pulse laser beam with a certain amount of pre-chirp compensation, said pre-chirp compensator comprising optical elements which cause components of the pulse laser beam to be emitted in order of wavelength such that shorter wavelengths are emitted earlier than longer wavelengths, a plurality of objective lenses adapted to be selectively placed on said optical path for collecting the pulse laser beam on the sample, the objective lenses including objective lenses having different optical path lengths, and a correcting mechanism including at least one flat plate optical element adapted to be detachably inserted into the optical path of said optical system, so as to cancel change in an optical path length of said optical system caused by replacement of the objective lenses having different optical path lengths.

18. The microscope according to claim 1, wherein said at least one optical correcting element comprises a plurality of optical correcting elements, and said plurality of optical correcting elements are adapted to be selectively placed on said optical path in accordance with which of said objective lenses is selectively placed on said optical path in a one-to-one corresponding relationship.

\* \* \* \* \*